(12) United States Patent
Chaki et al.

(10) Patent No.: US 9,573,868 B2
(45) Date of Patent: Feb. 21, 2017

(54) METHOD FOR PURIFYING CHLORINATED HYDROCARBON

(75) Inventors: Takehiro Chaki, Settsu (JP); Kazuhiro Takahashi, Settsu (JP); Hitoshi Yoshimi, Settsu (JP); Yoshinori Tanaka, Settsu (JP); Yuusuke Iwanaga, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/239,648

(22) PCT Filed: Sep. 13, 2012

(86) PCT No.: PCT/JP2012/074131
§ 371 (c)(1),
(2), (4) Date: Feb. 19, 2014

(87) PCT Pub. No.: WO2013/039260
PCT Pub. Date: Mar. 21, 2013

(65) Prior Publication Data
US 2014/0194656 A1     Jul. 10, 2014

Related U.S. Application Data

(60) Provisional application No. 61/535,013, filed on Sep. 15, 2011.

(51) Int. Cl.
| | | |
|---|---|---|
| *C07C 17/38* | (2006.01) | |
| *C07C 17/383* | (2006.01) | |
| *C07C 17/20* | (2006.01) | |
| *C07C 17/25* | (2006.01) | |

(52) U.S. Cl.
CPC .......... *C07C 17/383* (2013.01); *C07C 17/206* (2013.01); *C07C 17/25* (2013.01); *C07C 17/38* (2013.01); *Y02P 20/582* (2015.11)

(58) Field of Classification Search
CPC ....... C07C 17/38; C07C 17/383; C07C 17/395
USPC ................................ 570/178, 161
See application file for complete search history.

(56) References Cited

U.S. PATENT DOCUMENTS

| | | |
|---|---|---|
| 2,996,555 A | 8/1961 | Rausch |
| 2009/0240090 A1 | 9/2009 | Merkel et al. |
| 2012/0178977 A1 | 7/2012 | Merkel et al. |
| 2012/0184785 A1 | 7/2012 | Cottrell et al. |
| 2013/0338408 A1 | 12/2013 | Merkel et al. |

FOREIGN PATENT DOCUMENTS

| | | |
|---|---|---|
| EP | 2 098 499 | 9/2009 |
| JP | 2009227675 | 10/2009 |
| JP | 2009298781 | 12/2009 |
| JP | 2014510027 | 4/2014 |
| JP | 2014510716 | 5/2014 |
| WO | 2009/015317 | 1/2009 |
| WO | 2010/111067 | 9/2010 |
| WO | 2010/123148 | 10/2010 |
| WO | 2010/131766 | 11/2010 |
| WO | 2011/056411 | 5/2011 |
| WO | 2011/059078 | 5/2011 |
| WO | 2011/135416 | 11/2011 |

OTHER PUBLICATIONS

International Search Report issued Jul. 22, 2013 in International (PCT) Application No. PCT/JP2012/074131.

*Primary Examiner* — Elvis O Price
(74) *Attorney, Agent, or Firm* — Wenderoth, Lind & Ponack, L.L.P.

(57) ABSTRACT

The present invention provides a method for purifying chlorinated hydrocarbon(s), comprising cooling a mixture containing hydrogen fluoride and at least one chlorinated hydrocarbon selected from the group consisting of 2-chloro-3,3,3-trifluoropropene, 2,3-dichloro-3,3-difluoropropene, 1,2,3-trichloro-1,1-difluoropropane, and 1,1,1,2,3-pentachloropropane to cause liquid-liquid separation of the mixture into an upper liquid phase having a high hydrogen fluoride concentration and a lower liquid phase having a high chlorinated hydrocarbon concentration, and a method for purifying a chlorinated hydrocarbon, comprising subjecting the lower liquid phase obtained by the liquid-liquid separation to a distillation operation. According to the present invention, a chlorinated hydrocarbon can be purified by separating and removing hydrogen fluoride from a chlorinated hydrocarbon-hydrogen fluoride mixture under simple and economically advantageous conditions.

18 Claims, 2 Drawing Sheets

METHOD FOR PURIFYING CHLORINATED HYDROCARBON

This application is a National Stage of International Application No. PCT/JP2012/074131, filed Sep. 13, 2012, and it claims priority to U.S. Provisional Application No. 61/535,013, filed Sep. 15, 2011.

TECHNICAL FIELD

The present invention relates to a method for purifying one or more chlorinated hydrocarbons from a mixture containing hydrogen fluoride and at least one chlorinated hydrocarbon, such as a hydrochlorofluorocarbon and a hydrochlorocarbon.

BACKGROUND ART

Various methods are known as a method for producing fluorinated halogenated hydrocarbons, which are used as blowing agents, cleaning agents, refrigerants, etc. In most of these methods, halocarbons or halogenated hydrocarbons are used as a starting material, and are highly fluorinated by fluorination or a hydrogen fluoride (HF) addition reaction.

In this case, as a method for fluorinating halocarbons or halogenated hydrocarbons, a method in which halocarbons or halogenated hydrocarbons as a starting material are reacted with HF is known (Patent Literature 1). As a specific method, there is, for example, a method in which halocarbons or halogenated hydrocarbons as a starting material and hydrogen fluoride (HF) are supplied to a reactor packed with a catalyst, and subjected to fluorination treatment to obtain a highly fluorinated halogenated hydrocarbon.

With regard to a method for producing $CF_3CCl=CH_2$ (HCFO-1233xf), for example, among these methods, various methods have been reported. A method has been reported in which $CCl_3CHClCH_2Cl$ (HCC-240 db) is used as a starting material, and hydrogen fluoride (HF) is supplied in an amount exceeding the stoichiometric amount and reacted with the starting material (Patent Literature 2).

In this method, an outflow obtained from a reactor is a mixture containing not only the desired product, i.e., HCFO-1233xf, but also an equimolar or excess amount of HF relative to HCFO-1233xf. Furthermore, this product also contains, in addition to unreacted starting material HCC-240 db, other hydrochlorofluorocarbons as intermediates. To purify and use chlorinated hydrocarbons such as hydrochlorofluorocarbons including HCFO-1233xf, and starting material HCC-240 db from such a mixture, it is necessary to remove HF contained in the product. As a method therefor, a method in which a mixture containing chlorinated hydrocarbons and HF is treated with water or an alkali aqueous solution to absorb HF can be used. However, this method requires a large amount of water or alkali solution, resulting in the discharge of a large amount of industrial wastewater. It is thus undesirable in terms of environmental protection and production costs.

In addition, as another method for removing HF, there is a method in which HF is reacted with $H_2SO_4$ to collect HF as hydrofluoric-sulfuric acid. This method can be applied to removal of HF from a mixture of one or more chlorinated hydrocarbons and HF. However, in this method, the produced hydrofluoric-sulfuric acid is highly corrosive, and thus the materials of devices to be used are limited to highly corrosion-resistant materials. This leads to an increase in production costs.

Furthermore, in the case of the above method for removing HF, advanced technology is required to reuse the removed HF for a reaction. This leads to an increase in production costs even when the collected HF is recycled.

CITATION LIST

Patent Literature

PTL 1: U.S. Pat. No. 2,996,555
PTL 2: WO09/015,317

SUMMARY OF INVENTION

Technical Problem

The present invention has been accomplished in view of the foregoing problems; and its primary object is to provide a method for purifying one or more chlorinated hydrocarbons under economically advantageous conditions by separating and removing hydrogen fluoride from a mixture containing hydrogen fluoride and at least one chlorinated hydrocarbon, such as hydrochlorofluorocarbons (e.g., HCFO-1233xf) and hydrochlorocarbons, in a simple manner.

Solution to Problem

The present inventors conducted extensive research to achieve the above object. As a result, the inventors found a conventionally unknown phenomenon, that is, when a liquid mixture containing at least one specific chlorinated hydrocarbon and hydrogen fluoride (HF) (in particular, a product obtained when HCFO-1233xf is produced by fluorinating HCC-240 db) is cooled, the liquid mixture is separated into an upper liquid phase having a high HF concentration and a lower liquid phase having a high chlorinated hydrocarbon concentration. The inventors thus conceived that the concentration of hydrogen fluoride in the chlorinated hydrocarbon phase can be greatly reduced in a simple manner by conducting liquid-liquid separation using the above method. Furthermore, the inventors also found that when the lower liquid phase obtained by the liquid-liquid separation, which has a high chlorinated hydrocarbon concentration, is distilled to withdraw a fraction containing one or more chlorinated hydrocarbons and HF from the top of a distillation column, HF contained in the lower liquid phase is separated and removed, thus obtaining one or more chlorinated hydrocarbons substantially free of HF from the bottom of the column or a middle portion of the column. The present invention was accomplished as a result of further research based on these findings.

More specifically, the present invention provides the following method for purifying a chlorinated hydrocarbon.

Item 1. A method for purifying one or more chlorinated hydrocarbons, comprising cooling a mixture containing hydrogen fluoride and at least one chlorinated hydrocarbon selected from the group consisting of 2-chloro-3,3,3-trifluoropropene, 2,3-dichloro-3,3-difluoropropene, 1,2,3-trichloro-1,1-difluoropropane, and 1,1,1,2,3-pentachloropropane to cause liquid-liquid separation of the mixture into an upper liquid phase having a high hydrogen fluoride concentration and a lower liquid phase having a high chlorinated hydrocarbon concentration.

Item 2. The method according to Item 1, wherein the mixture containing the at least one chlorinated hydrocarbon and hydrogen fluoride is a product obtained when 2-chloro- 3,3,3-trifluoropropene is produced by fluorinating 1,1,1,2,3-pentachloropropane with hydrogen fluoride.

Item 3. The method according to Item 1, wherein the chlorinated hydrocarbon to be treated is 2-chloro-3,3,3-trifluoropropene.

Item 4. The method according to Item 1, wherein the chlorinated hydrocarbon to be treated is 2,3-dichloro-3,3-difluoropropene.

Item 5. The method according to Item 1, wherein the chlorinated hydrocarbon to be treated is 1,2,3-trichloro-1,1-difluoropropane.

Item 6. The method according to Item 1, wherein the chlorinated hydrocarbon to be treated is 1,1,1,2,3-pentachloropropane.

Item 7. A method for purifying one or more chlorinated hydrocarbons, comprising, after causing liquid-liquid separation into an upper liquid phase having a high hydrogen fluoride concentration and a lower liquid phase having a high chlorinated hydrocarbon concentration by the method of Item 1 or 2, subjecting the lower liquid phase having a high chlorinated hydrocarbon concentration to a distillation operation to withdraw a mixture containing one or more chlorinated hydrocarbons and hydrogen fluoride from the top of a distillation column, thereby obtaining one or more chlorinated hydrocarbons substantially free of hydrogen fluoride from the bottom of the distillation column or a middle portion of the distillation column.

Item 8. A method for purifying a chlorinated hydrocarbon, comprising, after causing liquid-liquid separation into an upper liquid phase having a high hydrogen fluoride concentration and a lower liquid phase having a high chlorinated hydrocarbon concentration by the method of any one of Items 3 to 6, subjecting the lower liquid phase having a high chlorinated hydrocarbon concentration to a distillation operation to withdraw a mixture containing the chlorinated hydrocarbon and hydrogen fluoride from the top of a distillation column, thereby obtaining the chlorinated hydrocarbon substantially free of hydrogen fluoride from the bottom of the distillation column.

Item 9. A method for purifying one or more chlorinated hydrocarbons, comprising recycling the mixture containing one or more chlorinated hydrocarbons and hydrogen fluoride and withdrawn from the top of the distillation column in the method of Item 7 or 8 into the mixture containing the at least one chlorinated hydrocarbon and hydrogen fluoride to be treated in Item 1.

The method for purifying one or more chlorinated hydrocarbons of the present invention is specifically described below.

Treatment Targets

The treatment target of the present invention is a mixture containing hydrogen fluoride (HF) and at least one chlorinated hydrocarbon selected from the group consisting of 2-chloro-3,3,3-trifluoropropene (HCFO-1233xf) represented by the chemical formula: $CF_3CCl=CH_2$; 2,3-dichloro-3,3-difluoropropene (HCFO-1232xf) represented by the chemical formula: $CClF_2CCl=CH_2$; 1,2,3-trichloro-1,1-difluoropropane (HCFC-242dc) represented by the chemical formula: $CClF_2CHClCHCl_2$; and 1,1,1,2,3-pentachloropropane (HCC-240 db) represented by the chemical formula: $CCl_3CHClCH_2Cl$.

Mixtures containing the above components can be obtained, for example, as a product obtained by fluorination treatment of halocarbons, a product obtained by fluorination treatment of chlorofluorohydrocarbon, etc. In the present invention, the types of mixtures to be treated are not particularly limited. Furthermore, the treatment target may also include a product obtained by combining the above-described treatments, and a product obtained by distilling the above products.

There is also no particular limitation on the ratio of 2-chloro-3,3,3-trifluoropropene (HCFO-1233xf), 2,3-dichloro-3,3-difluoropropene (HCFO-1232xf), 1,2,3-trichloro-1,1-difluoropropane (HCFC-242dc), and 1,1,1,2,3-pentachloropropane (HCC-240 db) included in the chlorinated hydrocarbons to be treated. A mixture containing only one chlorinated hydrocarbon among these may be used, or a mixture containing these chlorinated hydrocarbons at an optionally chosen ratio may be used.

As a representative example of the treatment target, a product obtained when 2-chloro-3,3,3-trifluoropropene (HCFO-1233xf) is produced by reacting hydrogen fluoride (HF) in an amount exceeding the stoichiometric amount with 1,1,1,2,3-pentachloropropane (HCC-240 db) can be mentioned. This product is a mixture containing not only the desired product, i.e., HCFO-1233xf, but also unreacted starting material HCC-240 db; and intermediates such as 2,3-dichloro-3,3-difluoropropene (HCFO-1232xf) and 1,2,3-trichloro-1,1-difluoropropane (HCFC-242dc).

The ratio of the chlorinated hydrocarbon (organic substance) and HF in the treatment target is also not particularly limited. Any mixture, regardless of the ratio, can be separated into a hydrogen fluoride-rich upper liquid phase and a chlorinated hydrocarbon (organic substance)-rich lower liquid phase by adjusting the cooling temperature in the below-described liquid-liquid separation step.

In addition, a mixture containing the chlorinated hydrocarbon(s) (organic substance) and HF may contain other components insofar as they do not interfere with the mechanism of the below-described liquid-liquid separation step and distillation step of the present invention.

Examples of such components include 1,1,2,3-tetrachloropropene (HCFO-1230xa) represented by $CH_2ClCCl=CCl_2$; 2,3,3-trichloro-3-fluoropropene (HCFO-1231xf) represented by $CCl_2FCCl=CH_2$; 1,2,3-trichloro-1-fluoropropene (E,Z-HCFO-1231xb) represented by $CH_2ClCCl=CClF$; 1,1,2-trichloro-3-fluoropropene (HCFO-1231xa) represented by $CH_2FCCl=CCl_2$; 1,3,3-trichloro-3-fluoropropene (E,Z-HCFO-1231zd) represented by $CCl_2FCH=CHCl$; 2,3-dichloro-1,1-difluoropropene (HCFO-1232xc) represented by $CH_2ClCCl=CF_2$; 1,1,2,3-tetrachloro-1-fluoropropane (HCFC-241 db) represented by $CCl_2FCHClCH_2Cl$; 1,2-dichloro-3,3,3-trifluoropropane (HCFC-243 db) represented by $CF_3CHClCH_2Cl$; 2-chloro-1,1,1,2-tetrafluoropropane (HCFC-244bb) represented by $CF_3CClFCH_3$; 1,1,1,2,3-pentafluoropropane (HFC-245eb) represented by $CF_3CHFCH_2F$; and 1,1,1,2,2-pentafluoropropane (HFC-245cb) represented by $CF_3CF_2CH_3$. A mixture containing these components can also be a treatment target in the method of the present invention.

Method for Separating Chlorinated Hydrocarbon and Hydrogen Fluoride

The treatment process in the method for purifying one or more chlorinated hydrocarbons of the present invention is specifically described below based on the flow diagram shown in FIG. 1.

(1) Liquid-Liquid Separation Step

First, in the present invention, a mixture containing hydrogen fluoride and at least one chlorinated hydrocarbon selected from the group consisting of 2-chloro-3,3,3-trifluoropropene (HCFO-1233xf), 2,3-dichloro-3,3-difluoropropene (HCFO-1232xf), 1,2,3-trichloro-1,1-difluoropropane (HCFC-242dc), and 1,1,1,2,3-pentachloropropane (HCC-240 db) is supplied to a liquid separation tank A, and the mixture is cooled to be separated into an upper liquid phase having a high HF concentration and a lower liquid phase having a high chlorinated hydrocarbon concentration.

In general, the HF concentration in the lower liquid phase can be reduced by lowering the cooling temperature. Hence, the cooling temperature is preferably as low as possible in order to separate the lower liquid phase with a high chlorinated hydrocarbon (organic substance) concentration. In addition, the lower the cooling temperature is, the shorter the relaxation time of phase separation is likely to be. Accordingly, the method of the present invention can be more effectively conducted when the cooling temperature is lower. However, when the cooling temperature is excessively lowered, the amount of energy required for cooling becomes large. Considering the above, it is preferred that the cooling temperature is generally about 15° C. to −40° C.

The specific cooling temperature may be suitably determined by the composition of the chlorinated hydrocarbon component(s) to be treated. For example, regarding a mixture containing only one chlorinated hydrocarbon, a suitable cooling temperature may be determined based on a liquid-liquid equilibrium curve of the chlorinated hydrocarbon and HF. Regarding a mixture containing two or more chlorinated hydrocarbons, cooling may be carried out under conditions corresponding to a cooling temperature suitable for the mixture of HF and the main component among the chlorinated hydrocarbons based on a liquid-liquid equilibrium curve of a mixture of HF and the main component.

For example, in a product obtained by fluorinating 1,1,1,2,3-pentachloropropane (HCC-240 db) with hydrogen fluoride, when the main component among chlorinated hydrocarbons is 2-chloro-3,3,3-trifluoropropene (HCFO-1233xf), the cooling temperature may be determined based on a cooling temperature suitable for a mixture containing HCFO-1233xf and hydrogen fluoride.

Note that the liquid-liquid equilibrium curve of a mixture of hydrogen fluoride and each chlorinated hydrocarbon component to be treated is as described below.

In general, by cooling in the aforementioned range, a chlorinated hydrocarbon-HF mixture phase (lower liquid phase) can be obtained, in which the mole fraction of HF is in a range of about 0.005 to 0.25 according to the composition of the chlorinated hydrocarbon component(s) to be treated. The HF-rich upper liquid phase in this step can be withdrawn from the liquid separation tank A; and reused, for example, as a starting material in a step of subjecting HCFO-1233xf to fluorination treatment to produce HFO-1234yf. In addition, if the HF-rich upper liquid phase is fed to a distillation column and subjected to another purification step, higher purity HF can be obtained.

(2) Distillation Step

Next, the lower liquid phase obtained by the above process is fed to a distillation column B, and distillation treatment is carried out.

The lower liquid phase obtained in the liquid-liquid separation step is a chlorinated hydrocarbon-HF mixture having a low HF concentration. By continuously withdrawing a chlorinated hydrocarbon-HF mixture from the top of the column by the above-described distillation operation, the HF concentration gradually decreases from the top of the column toward the bottom of the column, thus obtaining one or more chlorinated hydrocarbons substantially free of HF in the bottom of the column.

In addition, when two or more chlorinated hydrocarbons are contained, the number of plates of the distillation column can be increased to separate a particular chlorinated hydrocarbon from a middle portion of the distillation column according to its boiling point.

The distillation can be conducted by a common method under any pressure, i.e., increased pressure, ordinary pressure, or reduced pressure. The operation pressure in the distillation column may be determined by the boiling point and composition of a treatment target. It may be generally adjusted to a range of about −0.05 MPa·G to 2 MPa·G, preferably a range of 0 MPa·G to 1 MPa·G.

Specific distillation conditions such as, for example, column top temperature and column bottom temperature, may be determined according to the specific composition of the lower liquid phase obtained in the liquid-liquid separation step. They may be determined so that a chlorinated hydrocarbon-hydrogen fluoride mixture can be withdrawn from the top of the column during the distillation operation, and so that one or more chlorinated hydrocarbons substantially free of hydrogen fluoride can be obtained in the bottom of the column.

The chlorinated hydrocarbon-hydrogen fluoride mixture obtained from the top of the column may be recycled to the liquid-liquid separation step. This increases the purity of the desired chlorinated hydrocarbon.

Further, among the chlorinated hydrocarbon components, as to a component whose compatibility with HF is higher than its compatibility with the desired chlorinated hydrocarbon, the concentration of the component in the bottom of the column can be reduced by withdrawn the component from the top of the column. This enables an increase in the purity of the desired chlorinated hydrocarbon in the bottom of the column. For example, in the case where the main component of a product obtained when HCFO-1233xf is produced by fluorinating HCC-240 db is the desired substance, i.e., HCFO-1233xf, the purity of HCFO-1233xf in the bottom of the column can be increased by withdrawing, among components contained in the product, a component whose compatibility with HF is higher than its compatibility with HCFO-1233xf from the top of the column together with HF.

On the other hand, among the chlorinated hydrocarbon components, as to a component whose compatibility with HF is lower than its compatibility with the desired chlorinated hydrocarbon, the concentration of the component in a middle portion of the column or the bottom of the column can be reduced by withdrawing the component from the bottom of the column or the middle portion of the column according to its boiling point. This enables an increase in the purity of the desired chlorinated hydrocarbon in the middle portion of the column or the bottom of the column. For example, in the case where the desired substance is HCFO-1233xf, and a component whose compatibility with HCFO-1233xf is higher than its compatibility with HF is contained, if the boiling point of the component is higher than that of HCFO-1233xf, the component is concentrated in the bottom of the column, and thus the purity of HCFO-1233xf in a middle portion of the column can be increased. If the boiling point of the component is lower than that of HCFO-1233xf, the component is concentrated in a middle portion of the column, and thus the purity of HCFO-1233xf in the bottom of the column can be increased.

A mixture containing HCFO-1233xf as a main component obtained from the bottom of the column or a middle portion of the column can be used as is as a raw material, or subjected to common treatment such as distillation, liquid separation, extraction, and extractive distillation to be used as a raw material, for example, in a step of producing HFO-1234yf by conducting fluorination treatment.

Among mixtures of HF and each individual component included in the aforementioned chlorinated hydrocarbons, the treatment processes for a mixture of 2-chloro-3,3,3-trifluoropropene (HCFO-1233xf) and hydrogen fluoride, and a mixture of 2,3-dichloro-3,3-difluoropropene (HCFO-1232xf) and hydrogen fluoride are more specifically described below.

Method for Separating 2-Chloro-3,3,3-Trifluoropropene (HCFO-1233xf) and Hydrogen Fluoride (1) Liquid-Liquid Separation Step The operation method of a liquid-liquid separation step for a mixture containing HCFO-1233xf and hydrogen fluoride may be similar to that of the above-described liquid-liquid separation step for a mixture containing at least one chlorinated hydrocarbon and hydrogen fluoride. A mixture containing HCFO-1233xf and hydrogen fluoride may be supplied to a liquid separation tank, and the mixture may be cooled to be separated into an upper liquid phase having a high concentration of HF and a lower liquid phase having a high concentration of HCFO-1233xf.

FIG. 2 shows a liquid-liquid equilibrium curve of a mixture of HCFO-1233xf and HF at atmospheric pressure (0.1 MPa). As is clear from FIG. 2, the cooling temperature is preferably as low as possible, more preferably about 10° C. or less, in order to separate the lower liquid phase with a high concentration of HCFO-1233xf. In addition, as described above, the method of the present invention can be effectively conducted when the cooling temperature is lower; however, when the cooling temperature is excessively lowered, the amount of energy required for cooling becomes large. In view of economic efficiency, the cooling temperature is preferably not lower than about −40° C.

Cooling in such a temperature range enables a mixed liquid phase (lower liquid phase) of HCFO-1233xf and HF to be obtained in which the mole fraction of HF is in a range of about 0.1 to 0.05.

The HF-rich upper liquid phase obtained in this step can be withdrawn from the liquid separation tank A; and reused, for example, as a starting material in a step of subjecting HCFO-1233xf to fluorination treatment to produce HFO-1234yf.

(2) Distillation Step

The lower liquid phase obtained in the aforementioned liquid-liquid separation step is a mixture containing HCFO-1233xf and HF with a low concentration of HF. By continuously withdrawing a mixture containing HCFO-1233xf and HF from the top of a column by a distillation operation, the HF concentration gradually decreases from the top of the column toward the bottom of the column. Consequently, a component containing HCFO-1233xf substantially free of HF can be obtained in the bottom of the column.

The operation pressure in the distillation column may be adjusted to a range of about −0.05 MPa·G to 2 MPa·G, preferably a range of about 0 MPa·G to 1 MPa·G.

Distillation conditions such as column top temperature and column bottom temperature may be determined so that a mixture containing HCFO-1233xf and hydrogen fluoride can be withdrawn from the top of the column during the distillation operation, and so that HCFO-1233xf substantially free of hydrogen fluoride can be obtained in the bottom of the column.

Method for Separating 2,3-Dichloro-3,3-Difluoropropene (HCFO-1232xf) and Hydrogen Fluoride (1) Liquid-Liquid Separation Step An operation method in a liquid-liquid separation step for a mixture containing HCFO-1232xf and hydrogen fluoride may also be similar to that in the above-mentioned liquid-liquid separation step for a mixture containing at least one chlorinated hydrocarbon and hydrogen fluoride. A mixture containing HCFO-1232xf and hydrogen fluoride may be supplied to a liquid separation tank, and the mixture may be cooled to be separated into an upper liquid phase having a high concentration of HF and a lower liquid phase having a high concentration of HCFO-1232xf.

FIG. 3 shows a liquid-liquid equilibrium curve of a mixture of HCFO-1232xf and HF at atmospheric pressure (0.1 MPa). As is clear from FIG. 3, the cooling temperature is preferably as low as possible, more preferably about 15° C. or less in order to separate the lower liquid phase having a high concentration of HCFC-1232xf. In addition, as described above, the method of the present invention can be effectively conducted when the cooling temperature is lower; however, when the cooling temperature is excessively lowered, the amount of energy required for cooling becomes large. Accordingly, in view of economic efficiency, the cooling temperature is preferably not lower than about −40° C.

Cooling in such a temperature range enables a mixed liquid phase (lower liquid phase) of HCFO-1232xf and HF to be obtained in which the mole fraction of HF is in a range of about 0.02 to 0.05.

The HF-rich upper liquid phase obtained in this step can be withdrawn from the liquid separation tank A; and reused, for example, as a starting material in a step of subjecting HCFO-1232xf to fluorination treatment to produce HCFO-1233xf or HFO-1234yf.

(2) Distillation Step

The lower liquid phase obtained in the above-mentioned liquid-liquid separation step is a mixture containing HCFO-1232xf and HF with a low concentration of HF. By continuously withdrawing a mixture containing HCFO-1232xf and HF from the top of a column by a distillation operation, the HF concentration gradually decreases from the top of the column toward the bottom of the column, and a component containing HCFO-1232xf substantially free of HF can be obtained in the bottom of the column.

The operation pressure in the distillation column may be adjusted to a range of about −0.05 MPa·G to 2 MPa·G, preferably a range of about 0 MPa·G to 1 MPa·G.

Distillation conditions such as column top temperature and column bottom temperature may be determined so that a mixture containing HCFO-1232xf and hydrogen fluoride can be withdrawn from the top of the column during the distillation operation, and so that HCFO-1232xf substantially free of hydrogen fluoride can be obtained in the bottom of the column.

Advantageous Effects of Invention

According to the method of the present invention, one or more chlorinated hydrocarbons having a greatly reduced hydrogen fluoride concentration can be obtained in a very simple manner in which a mixture containing at least one chlorinated hydrocarbon and hydrogen fluoride is cooled to cause liquid-liquid separation. Furthermore, by subjecting a mixture (lower liquid phase) obtained by the liquid-liquid separation, which has a reduced hydrogen fluoride concentration, to a distillation operation, one or more chlorinated hydrocarbons substantially free of hydrogen fluoride can be obtained; thus, chlorinated hydrocarbon purification is enabled by separating and removing hydrogen fluoride under simple and economically advantageous conditions.

In particular, in the case where a product obtained when HCFO-1233xf is produced by fluorinating HCC-240 db is a treatment target, hydrogen fluoride can be separated from the product by a simple method; the purity of the desired product, i.e., HCFO-1233xf, can be improved; and, furthermore, a by-product or unreacted starting material can be effectively used.

DESCRIPTION OF EMBODIMENTS

Examples are given below to illustrate the present invention in more detail.

Example 1

Figure 1:
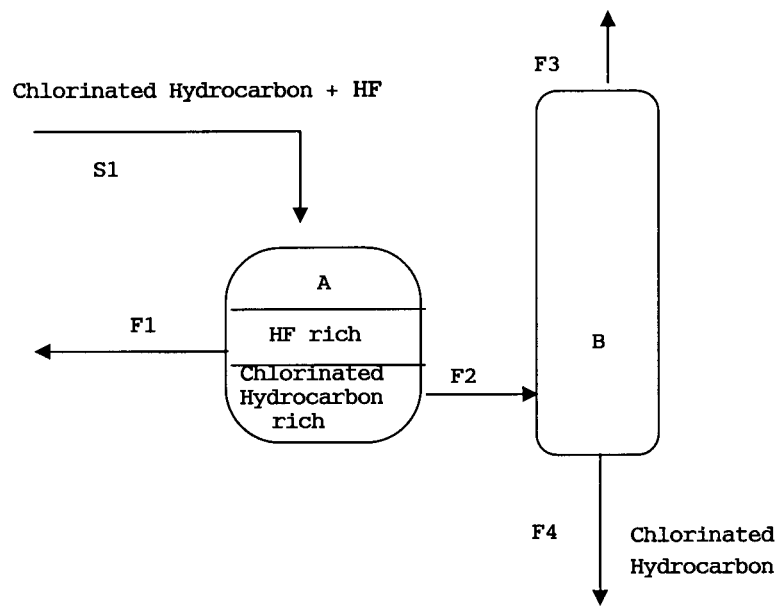
FIG. 1 is a flow diagram of an example of the method of the present invention, in which a chlorinated hydrocarbon-HF mixture is a treatment target; this example does not comprise a step of recycling a mixture obtained from the top of the column after the distillation step to the liquid-liquid separation step.
Figure 2:
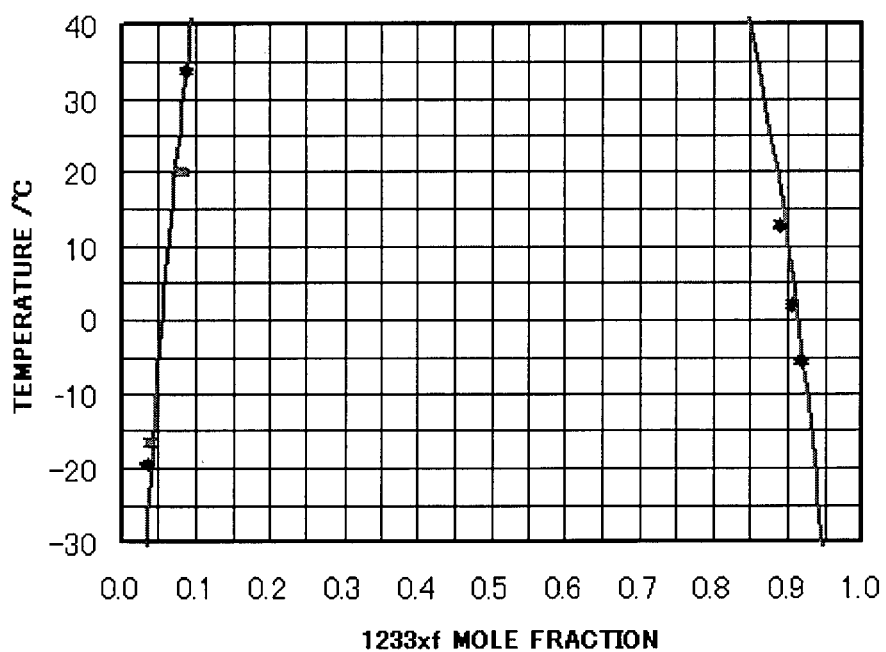
FIG. 2 is a liquid-liquid equilibrium curve of a mixture of HCFO-1233xf and HF.
Figure 3:
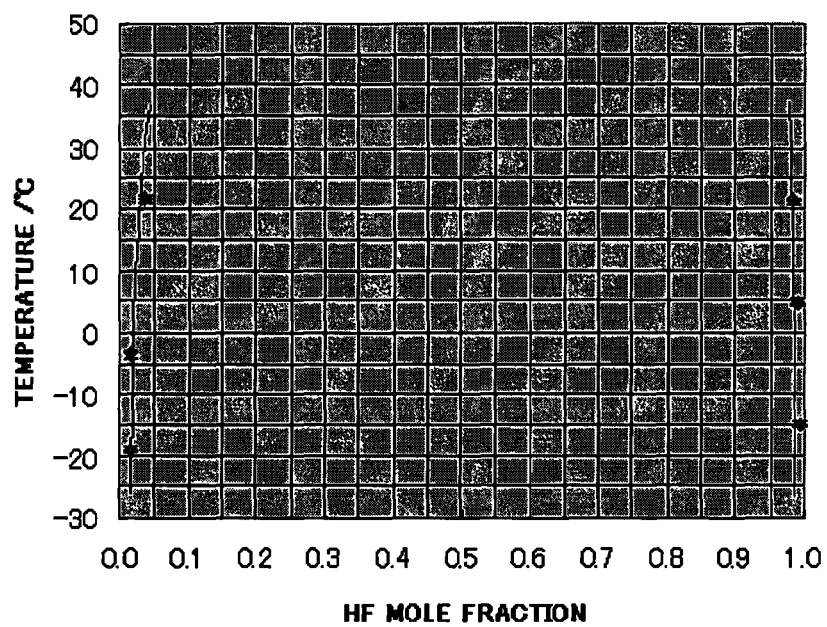
FIG. 3 is a liquid-liquid equilibrium curve of a mixture of HCFO-1232xf and HF.

HF was separated from a mixture containing various chlorinated hydrocarbons and HF to obtain the desired substance, i.e., HCFO-1233xf, by the following method. This method is described based on the flow diagram shown in FIG. 1.

First, a mixed gas of chlorinated hydrocarbons and HF having a composition shown in Table 1 below was condensed and then introduced into a liquid separation tank A at 31.4° C. (S1). In the liquid separation tank, the resulting liquid mixture was cooled to −20° C., and separated into a first fraction (F1) containing HF as a main component and a second fraction (F2) containing the chlorinated hydrocarbons as a main component.

The second fraction (F2) was supplied to the next distillation step, and a distillation operation was carried out. From the top of a column, a HF-chlorinated hydrocarbon mixture was withdrawn as a third fraction (F3). In addition, a fourth fraction (F4) substantially free of HF was withdrawn from the bottom of the column and supplied to the next step. In Table 1 below, the column top temperature in the distillation operation was indicated as T1, while the column bottom temperature in the distillation operation was indicated as T2. Further, the process of the liquid-liquid separation step and the distillation step was conducted under a pressure of 0.7 MPa·G.

Table 1 shows the compositions of the components in each of the steps.

TABLE 1

| Experiment | | Flow Rate kg/hr | | | | | Temperature ° C. | |
| --- | --- | --- | --- | --- | --- | --- | --- | --- |
| No. | Component | S1 | F1 | F2 | F3 | F4 | T1 | T2 |
| 1 | HF | 9.50 | 9.50 | 0.0084 | 0.0084 | 0 | 69.1 | 100.9 |
| | HCFO-1233xf | 2.61 | 1.65 | 0.96 | 0.08 | 0.88 | | |
| | HCFO-1232xf | 0.367 | 0.100 | 0.265 | 0 | 0.265 | | |
| | HCFC242dc | 0.367 | 0.076 | 0.291 | 0 | 0.291 | | |
| | HCC-240db | 0.108 | 0.106 | 0.002 | 0 | 0.002 | | |

As is clear from the results, shown in Table 1, this process enables separation of chlorinated hydrocarbons and HF without employing a method used in conventional techniques that uses highly corrosive sulfuric acid.

Example 2

Figure 4:
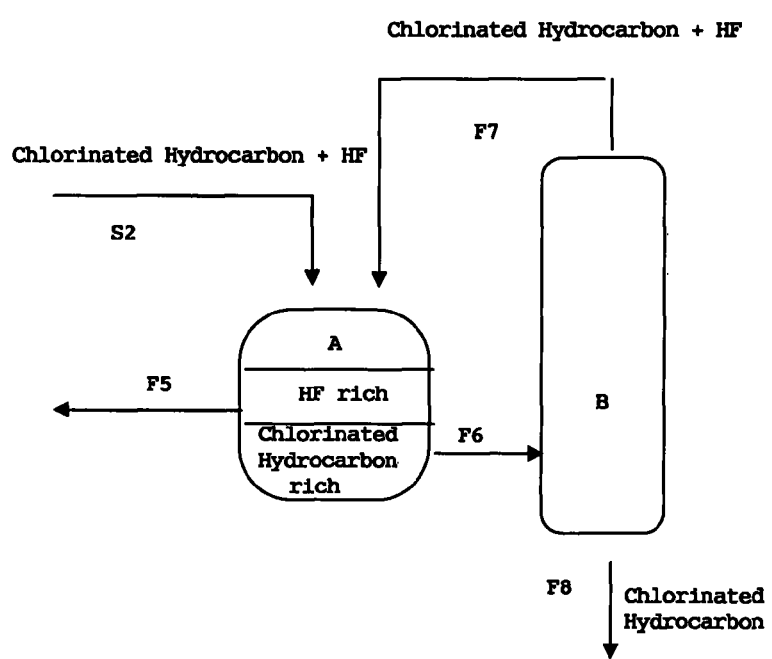
FIG. 4 is a flow diagram of an example of the method of the present invention, in which a chlorinated hydrocarbon-HF mixture is a treatment target; this example comprises a step of recycling a mixture obtained from the top of the column after the distillation step to the liquid-liquid separation step.

HF was separated from a mixture containing various chlorinated hydrocarbons and HF by the following method. This method is described based on the flow diagram shown in FIG. 4.

First, each mixed gas of at least one chlorinated hydrocarbon and HF having a composition shown in the column of each experiment number in Table 2 below was condensed and then introduced into a liquid separation tank A at 31.4° C. (S2). In the liquid separation tank, the resulting liquid mixture was cooled to −20° C., and separated into a fifth fraction (F5) containing HF as a main component and a sixth fraction (F6) containing the chlorinated hydrocarbon as a main component.

The sixth fraction (F6) was supplied to the next distillation step, and a distillation operation was carried out. From the top of a column, a HF-chlorinated hydrocarbon mixture was withdrawn and recycled as a seventh fraction (F7) to the liquid separation tank. An eighth fraction (F8) substantially free of HF was withdrawn from the bottom of the column and supplied to the next step. In Table 2 below, the column top temperature in the distillation operation was indicated as T3, while the column bottom temperature in the distillation operation was indicated as T4. Further, the process of the liquid-liquid separation step and the distillation step was conducted under a pressure of 0.7 MPa·G.

Table 2 shows the compositions of the components in each of the steps.

TABLE 2

| Experiment No. | Component | Flow Rate kg/hr | | | | | Temperature ° C. | |
|---|---|---|---|---|---|---|---|---|
| | | S2 | F5 | F6 | F7 | F8 | T3 | T4 |
| 2 | HF | 9.50 | 9.50 | 0.0079 | 0.0079 | 0.0 | 73.1 | 86.0 |
| | HCFO-1233xf | 3.26 | 2.69 | 0.70 | 0.13 | 0.57 | | |
| 3 | HF | 9.50 | 9.50 | 0.0069 | 0.0069 | 0 | 136.8 | 139.4 |
| | HCFO-1232xf | 3.67 | 0.45 | 4.18 | 0.96 | 3.22 | | |
| 4 | HF | 9.50 | 9.50 | 0.0022 | 0.0022 | 0.0 | 206.7 | 208.4 |
| | HCFC-242dc | 4.58 | 0.36 | 4.84 | 0.61 | 4.23 | | |
| 5 | HF | 9.50 | 9.50 | 0.011 | 0.011 | 0 | 78.7 | 103.0 |
| | HCFO-1233xf | 2.61 | 1.71 | 1.27 | 0.37 | 0.90 | | |
| | HCFO-1232xf | 0.367 | 0.085 | 0.281 | 0 | 0.281 | | |
| | HCFC-242dc | 0.458 | 0.078 | 0.38 | 0 | 0.38 | | |
| 6 | HF | 9.50 | 9.50 | 0.0088 | 0.0088 | 0 | 68.9 | 100.3 |
| | HCFO-1233xf | 2.61 | 1.68 | 1.01 | 0.08 | 0.93 | | |
| | HCFO-1232xf | 0.367 | 0.100 | 0.267 | 0 | 0.267 | | |
| | HCFC242dc | 0.364 | 0.074 | 0.293 | 0 | 0.293 | | |
| | HCC-240db | 0.108 | 0.009 | 0.099 | 0 | 0.099 | | |

As is clear from the results shown in Table 2, the above-described process enables effective separation of chlorinated hydrocarbons and HF without using sulfuric acid. In particular, a comparison of the results in Experiment 1 of Example 1 and Experiment 6 of Example 2, in which the amounts of starting materials supplied and operation conditions are almost the same, reveals that the flow rate of HCFO-1233xf obtained in the bottom of the column in the distillation step is greater in Experiment 6, which comprises a step of recycling a mixture obtained from the top of the column in the distillation step to the liquid-liquid separation step. This indicates that by comprising a step of recycling a mixture obtained from the top of the column in the distillation step to the liquid-liquid separation step, the separation of chlorinated hydrocarbons and hydrogen fluoride can be effectively carried out.

The invention claimed is:

1. A method for purifying one or more chlorinated hydrocarbons, comprising cooling a mixture consisting essentially of hydrogen fluoride and at least one chlorinated hydrocarbon selected from the group consisting of 2-chloro-3,3,3-trifluoropropene, 2,3-dichloro-3,3-difluoropropene, 1,2,3-trichloro-1,1-difluoropropane, and 1,1,1,2,3-pentachloropropane, to cause liquid-liquid separation of the mixture into an upper liquid phase having a high hydrogen fluoride concentration and lower liquid phase having a high chlorinated hydrocarbon concentration.

2. The method according to claim 1, wherein the mixture containing the at least one chlorinated hydrocarbon and hydrogen fluoride is a product obtained when 2-chloro-3,3,3-trifluoropropene is produced by fluorinating 1,1,1,2,3-pentachloropropane with hydrogen fluoride.

3. The method according to claim 1, wherein the chlorinated hydrocarbon to be treated is 2-chloro-3,3,3-trifluoropropene.

4. The method according to claim 1, wherein the chlorinated hydrocarbon to be treated is 2,3-dichloro-3,3-difluoropropene.

5. The method according to claim 1, wherein the chlorinated hydrocarbon to be treated is 1,2,3-trichloro-1,1-difluoropropane.

6. The method according to claim 1, wherein the chlorinated hydrocarbon to be treated is 1,1,1,2,3-pentachloropropane.

7. A method for purifying one or more chlorinated hydrocarbons, comprising, after causing liquid-liquid separation into an upper liquid phase having a high hydrogen fluoride concentration and a lower liquid phase having a high chlorinated hydrocarbon concentration by the method of claim 1, subjecting the lower liquid phase having a high chlorinated hydrocarbon concentration to a distillation operation to withdraw a mixture containing one or more chlorinated hydrocarbons and hydrogen fluoride from the top of a distillation column, thereby obtaining one or more chlorinated hydrocarbons substantially free of hydrogen fluoride from the bottom of the distillation column or a middle portion of the distillation column.

8. A method for purifying a chlorinated hydrocarbon, comprising, after causing liquid-liquid separation into an upper liquid phase having a high hydrogen fluoride concentration and a lower liquid phase having a high chlorinated hydrocarbon concentration by the method of claim 3, subjecting the lower liquid phase having a high chlorinated hydrocarbon concentration to a distillation operation to withdraw a mixture containing the chlorinated hydrocarbon and hydrogen fluoride from the top of a distillation column, thereby obtaining the chlorinated hydrocarbon substantially free of hydrogen fluoride from the bottom of the distillation column.

9. A method for purifying one or more chlorinated hydrocarbons, comprising recycling the mixture containing one or more chlorinated hydrocarbons and hydrogen fluoride and withdrawn from the top of the distillation column in the method of claim 7 into the mixture containing the at least one chlorinated hydrocarbon and hydrogen fluoride to be treated in a method for purifying one or more chlorinated hydrocarbons, comprising cooling a mixture containing hydrogen fluoride and at least one chlorinated hydrocarbon selected from the group consisting of 2-chloro-3,3,3-trifluoropropene, 2,3-dichloro-3,3-difluoropropene, 1,2,3-trichloro-1,1-difluoropropane, and 1,1,1,2,3-pentachloropropane to cause liquid-liquid separation of the mixture into an upper liquid phase having a high hydrogen fluoride concentration and a lower liquid phase having a high chlorinated hydrocarbon concentration.

10. A method for purifying one or more chlorinated hydrocarbons, comprising, after causing liquid-liquid separation into an upper liquid phase having a high hydrogen fluoride concentration and a lower liquid phase having a high chlorinated hydrocarbon concentration by the method of claim 2, subjecting the lower liquid phase having a high chlorinated hydrocarbon concentration to a distillation operation to withdraw a mixture containing one or more chlorinated hydrocarbons and hydrogen fluoride from the top of a distillation column, thereby obtaining one or more chlorinated hydrocarbons substantially free of hydrogen fluoride from the bottom of the distillation column or a middle portion of the distillation column.

11. A method for purifying a chlorinated hydrocarbon, comprising, after causing liquid-liquid separation into an upper liquid phase having a high hydrogen fluoride concentration and a lower liquid phase having a high chlorinated hydrocarbon concentration by the method of claim 4, subjecting the lower liquid phase having a high chlorinated hydrocarbon concentration to a distillation operation to withdraw a mixture containing the chlorinated hydrocarbon and hydrogen fluoride from the top of a distillation column, thereby obtaining the chlorinated hydrocarbon substantially free of hydrogen fluoride from the bottom of the distillation column.

12. A method for purifying a chlorinated hydrocarbon, comprising, after causing liquid-liquid separation into an upper liquid phase having a high hydrogen fluoride concentration and a lower liquid phase having a high chlorinated hydrocarbon concentration by the method of claim 5, subjecting the lower liquid phase having a high chlorinated hydrocarbon concentration to a distillation operation to withdraw a mixture containing the chlorinated hydrocarbon and hydrogen fluoride from the top of a distillation column, thereby obtaining the chlorinated hydrocarbon substantially free of hydrogen fluoride from the bottom of the distillation column.

13. A method for purifying a chlorinated hydrocarbon, comprising, after causing liquid-liquid separation into an upper liquid phase having a high hydrogen fluoride concentration and a lower liquid phase having a high chlorinated hydrocarbon concentration by the method of claim 6, subjecting the lower liquid phase having a high chlorinated hydrocarbon concentration to a distillation operation to withdraw a mixture containing the chlorinated hydrocarbon and hydrogen fluoride from the top of a distillation column, thereby obtaining the chlorinated hydrocarbon substantially free of hydrogen fluoride from the bottom of the distillation column.

14. A method for purifying one or more chlorinated hydrocarbons, comprising recycling the mixture containing one or more chlorinated hydrocarbons and hydrogen fluoride and withdrawn from the top of the distillation column in the method of claim 8 into the mixture containing the at least one chlorinated hydrocarbon and hydrogen fluoride to be treated in a method for purifying one or more chlorinated hydrocarbons, comprising cooling a mixture containing hydrogen fluoride and at least one chlorinated hydrocarbon selected from the group consisting of 2-chloro-3,3,3-trifluoropropene, 2,3-dichloro-3,3-difluoropropene, 1,2,3-trichloro-1,1-difluoropropane, and 1,1,1,2,3-pentachloropropane to cause liquid-liquid separation of the mixture into an upper liquid phase having a high hydrogen fluoride concentration and a lower liquid phase having a high chlorinated hydrocarbon concentration.

15. A method for purifying one or more chlorinated hydrocarbons, comprising recycling the mixture containing one or more chlorinated hydrocarbons and hydrogen fluoride and withdrawn from the top of the distillation column in the method of claim 10 into the mixture containing the at least one chlorinated hydrocarbon and hydrogen fluoride to be treated in a method for purifying one or more chlorinated hydrocarbons, comprising cooling a mixture containing hydrogen fluoride and at least one chlorinated hydrocarbon selected from the group consisting of 2-chloro-3,3,3-trifluoropropene, 2,3-dichloro-3,3-difluoropropene, 1,2,3-trichloro-1,1-difluoropropane, and 1,1,1,2,3-pentachloropropane to cause liquid-liquid separation of the mixture into an upper liquid phase having a high hydrogen fluoride concentration and a lower liquid phase having a high chlorinated hydrocarbon concentration.

16. A method for purifying one or more chlorinated hydrocarbons, comprising recycling the mixture containing one or more chlorinated hydrocarbons and hydrogen fluoride and withdrawn from the top of the distillation column in the method of claim 11 into the mixture containing the at least one chlorinated hydrocarbon and hydrogen fluoride to be treated in a method for purifying one or more chlorinated hydrocarbons, comprising cooling a mixture containing hydrogen fluoride and at least one chlorinated hydrocarbon selected from the group consisting of 2-chloro-3,3,3-trifluoropropene, 2,3-dichloro-3,3-difluoropropene, 1,2,3-trichloro-1,1-difluoropropane, and 1,1,1,2,3-pentachloropropane to cause liquid-liquid separation of the mixture into an upper liquid phase having a high hydrogen fluoride concentration and a lower liquid phase having a high chlorinated hydrocarbon concentration.

17. A method for purifying one or more chlorinated hydrocarbons, comprising recycling the mixture containing one or more chlorinated hydrocarbons and hydrogen fluoride and withdrawn from the top of the distillation column in the method of claim 12 into the mixture containing the at least one chlorinated hydrocarbon and hydrogen fluoride to be treated in a method for purifying one or more chlorinated hydrocarbons, comprising cooling a mixture containing hydrogen fluoride and at least one chlorinated hydrocarbon selected from the group consisting of 2-chloro-3,3,3-trifluoropropene, 2,3-dichloro-3,3-difluoropropene, 1,2,3-trichloro-1,1-difluoropropane, and 1,1,1,2,3-pentachloropropane to cause liquid-liquid separation of the mixture into an upper liquid phase having a high hydrogen fluoride concentration and a lower liquid phase having a high chlorinated hydrocarbon concentration.

18. A method for purifying one or more chlorinated hydrocarbons, comprising recycling the mixture containing one or more chlorinated hydrocarbons and hydrogen fluoride and withdrawn from the top of the distillation column in the method of claim 13 into the mixture containing the at least one chlorinated hydrocarbon and hydrogen fluoride to be treated in a method for purifying one or more chlorinated hydrocarbons, comprising cooling a mixture containing hydrogen fluoride and at least one chlorinated hydrocarbon selected from the group consisting of 2-chloro-3,3,3-trifluoropropene, 2,3-dichloro-3,3-difluoropropene, 1,2,3-trichloro-1,1-difluoropropane, and 1,1,1,2,3-pentachloropropane to cause liquid-liquid separation of the mixture into an upper liquid phase having a high hydrogen fluoride concentration and a lower liquid phase having a high chlorinated hydrocarbon concentration.

\* \* \* \* \*